(12) United States Patent
Morton

(10) Patent No.: US 8,579,506 B2
(45) Date of Patent: Nov. 12, 2013

(54) GANTRY SCANNER SYSTEMS

(75) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 337 days.

(21) Appl. No.: 12/993,832

(22) PCT Filed: May 20, 2009

(86) PCT No.: PCT/GB2009/001277
§ 371 (c)(1),
(2), (4) Date: Feb. 10, 2011

(87) PCT Pub. No.: WO2009/141615
PCT Pub. Date: Nov. 26, 2009

(65) Prior Publication Data
US 2011/0142203 A1  Jun. 16, 2011

(30) Foreign Application Priority Data
May 20, 2008  (GB) .................................. 0809110.0

(51) Int. Cl.
*H05G 1/06* (2006.01)

(52) U.S. Cl.
USPC ......................................... 378/194; 378/198

(58) Field of Classification Search
USPC .............................. 378/57, 193, 194, 197, 198
See application file for complete search history.

(56) References Cited

U.S. PATENT DOCUMENTS

| | | | |
|---|---|---|---|
| 2,831,123 A | 4/1958 | Daly | |
| 3,766,387 A | 10/1973 | Heffan et al. | |
| 3,770,955 A | 11/1973 | Tomita et al. | |
| 3,784,837 A | 1/1974 | Holmstrom | |
| RE28,544 E | 9/1975 | Stein et al. | |
| 3,904,923 A | 9/1975 | Schwartz | |
| 4,047,035 A | 9/1977 | Dennhoven et al. | |
| 4,139,771 A | 2/1979 | Dennhoven et al. | |
| 4,210,811 A | 7/1980 | Dennhoven et al. | |
| 4,216,499 A | 8/1980 | Kunze et al. | |
| 4,366,382 A | 12/1982 | Kotowski | |
| 4,430,568 A | 2/1984 | Yoshida et al. | |
| 4,566,113 A | 1/1986 | Donges et al. | |
| 4,599,740 A | 7/1986 | Cable | |
| 4,626,688 A | 12/1986 | Barnes | |
| 4,641,330 A | 2/1987 | Herwig et al. | |

(Continued)

FOREIGN PATENT DOCUMENTS

| | | |
|---|---|---|
| EP | 0287707 | 11/1982 |
| EP | 00077018 | 4/1983 |

(Continued)

OTHER PUBLICATIONS

International Search Report PCT/GB2009/000515, Feb. 23, 2010, Rapiscan Security Products, Inc.

(Continued)

*Primary Examiner* — Jurie Yun

(74) *Attorney, Agent, or Firm* — Novel IP

(57) ABSTRACT

A gantry scanner system includes a radiation source, a plurality of detectors and a support frame supporting the detectors. The support frame includes an elongate support member arranged to support the detectors, cable support means arranged to support power cables or signal cables connected to the detectors, and cover means arranged to cover the support member, the cable support means and the detectors.

17 Claims, 4 Drawing Sheets

(56) References Cited

U.S. PATENT DOCUMENTS

| | | |
|---|---|---|
| 4,709,382 A | 11/1987 | Sones |
| 4,736,401 A | 4/1988 | Donges et al. |
| 4,788,704 A | 11/1988 | Donges et al. |
| 4,817,123 A | 3/1989 | Sones et al. |
| 4,825,454 A | 4/1989 | Annis et al. |
| 4,872,188 A | 10/1989 | Lauro et al. |
| 4,884,289 A | 11/1989 | Glockmann et al. |
| 4,979,202 A | 12/1990 | Siczek et al. |
| 4,991,189 A | 2/1991 | Boomgaarden et al. |
| 5,022,062 A | 6/1991 | Annis |
| 5,065,418 A | 11/1991 | Bermbach et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,221,843 A | 6/1993 | Alvarez |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis et al. |
| 5,313,511 A | 5/1994 | Annis et al. |
| 5,367,552 A | 11/1994 | Peschmann |
| 5,379,334 A | 1/1995 | Zimmer et al. |
| 5,493,596 A | 2/1996 | Annis |
| 5,548,123 A | 8/1996 | Perez-Mendez et al. |
| 5,638,420 A | 6/1997 | Armistead |
| 5,638,817 A * | 6/1997 | Morgan et al. ............... 600/425 |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,692,028 A | 11/1997 | Geus et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,974,111 A | 10/1999 | Krug et al. |
| 6,031,888 A * | 2/2000 | Ivan et al. ..................... 378/20 |
| 6,031,890 A | 2/2000 | Bermbach et al. |
| 6,058,158 A | 5/2000 | Eiler |
| 6,067,344 A | 5/2000 | Grodzins et al. |
| 6,081,580 A | 6/2000 | Grodzins et al. |
| 6,094,472 A | 7/2000 | Smith |
| 6,151,381 A | 11/2000 | Grodzins et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,218,943 B1 | 4/2001 | Ellenbogen |
| 6,249,567 B1 | 6/2001 | Rothschild et al. |
| 6,252,929 B1 | 6/2001 | Swift et al. |
| 6,256,369 B1 | 7/2001 | Lai |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,320,933 B1 | 11/2001 | Grodzins et al. |
| 6,356,620 B1 | 3/2002 | Rothschild et al. |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,453,003 B1 | 9/2002 | Springer et al. |
| 6,453,007 B2 | 9/2002 | Adams et al. |
| 6,456,684 B1 | 9/2002 | Mun et al. |
| 6,459,761 B1 | 10/2002 | Grodzins et al. |
| 6,459,764 B1 | 10/2002 | Chalmers et al. |
| 6,473,487 B1 | 10/2002 | Le |
| RE37,899 E | 11/2002 | Grodzins et al. |
| 6,483,894 B2 | 11/2002 | Hartick et al. |
| 6,507,025 B1 | 1/2003 | Verbinski et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,563,903 B2 | 5/2003 | Kang et al. |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,636,581 B2 | 10/2003 | Sorenson |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,665,433 B2 | 12/2003 | Roder |
| 6,763,635 B1 | 7/2004 | Lowman |
| 6,785,357 B2 | 8/2004 | Bernardi et al. |
| 6,812,426 B1 | 11/2004 | Kotowski et al. |
| 6,816,571 B2 | 11/2004 | Bijjani et al. |
| 6,837,422 B1 | 1/2005 | Meder |
| 6,839,403 B1 | 1/2005 | Kotowski et al. |
| 6,843,599 B2 | 1/2005 | Le et al. |
| 6,920,197 B2 | 7/2005 | Kang et al. |
| 7,039,159 B2 | 5/2006 | Muenchau et al. |
| 7,154,989 B2 * | 12/2006 | Ueno et al. ..................... 378/19 |
| 7,166,844 B1 | 1/2007 | Gormley et al. |
| 7,207,713 B2 | 4/2007 | Lowman |
| 7,486,768 B2 * | 2/2009 | Allman et al. ................. 378/57 |
| 2004/0017888 A1 | 1/2004 | Seppi et al. |
| 2004/0086078 A1 | 5/2004 | Adams et al. |
| 2004/0125914 A1 | 7/2004 | Kang et al. |
| 2004/0141584 A1 | 7/2004 | Bernardi et al. |
| 2004/0258198 A1 | 12/2004 | Carver et al. |
| 2005/0117700 A1 | 6/2005 | Peschmann |
| 2005/0135668 A1 | 6/2005 | Polichar et al. |
| 2005/0156734 A1 | 7/2005 | Zerwekh et al. |
| 2005/0157842 A1 | 7/2005 | Agrawal et al. |
| 2005/0169421 A1 | 8/2005 | Muenchau et al. |
| 2006/0284094 A1 | 12/2006 | Inbar |
| 2007/0110215 A1 | 5/2007 | Hu et al. |
| 2007/0172129 A1 | 7/2007 | Tortora et al. |
| 2007/0210255 A1 | 9/2007 | Bjorkholm |
| 2007/0269005 A1 | 11/2007 | Chalmers et al. |
| 2007/0280416 A1 | 12/2007 | Bendahan et al. |
| 2007/0280502 A1 | 12/2007 | Paresi et al. |
| 2007/0286337 A1 | 12/2007 | Wang et al. |
| 2008/0044801 A1 | 2/2008 | Modica et al. |
| 2008/0304622 A1 | 12/2008 | Morton |

FOREIGN PATENT DOCUMENTS

| | | |
|---|---|---|
| EP | 0176314 | 4/1986 |
| EP | 0919186 | 6/1999 |
| EP | 1413898 | 4/2004 |
| GB | 2255634 | 11/1992 |
| WO | WO9855851 | 10/1998 |
| WO | WO2006/036076 | 4/2006 |
| WO | WO2006/045019 | 4/2006 |
| WO | WO2006/078691 | 7/2006 |
| WO | WO2007/051092 | 5/2007 |
| WO | WO 2008/017983 | 2/2008 |

OTHER PUBLICATIONS

Search Report PCT/GB2009/000497, Jan. 26, 2010, Rapiscan Security Products, Inc.

(56) References Cited

OTHER PUBLICATIONS

International Search Report PCT/GB2009/150416, Dec. 17, 2009, Rapiscan Security Products.
Search Report for WO2009/106847, Sep. 3, 2009, Rapiscan Security Products.
International Search Report PCT/GB2009/001277, May 20, 2008, Rapiscan Systems, Inc.
"Mobile X-Ray Inspection Systems", Internet Citation, Feb. 12, 2007, pp. 1-2, URL:http://web.archive.org/web/20070212000928/http://www.bombdetection.com/cat_details.php?catid=20>.
Molchanov et al., "Nanosecond Gated Optical Sensors for Ocean Optic Applications," Sensors Applications Symposium, 2006, Proceedings of the 2006 IEEE, Feb. 7, 2006, 147-150.

\* cited by examiner

GANTRY SCANNER SYSTEMS

CROSS-REFERENCE TO RELATED APPLICATIONS

The present application is a national stage application of PCT/GB2009/001277, filed on May 20, 2009, which further relies on Great Britain Patent Application Number 0809110.0, filed on May 20, 2008, for priority.

FIELD OF THE INVENTION

The present invention relates to scanners and in particular to gantry scanner systems. It has particular application in cargo scanners, but can be used with scanners in other fields.

BACKGROUND

There is a requirement to screen cargo items for the detection of illicit materials and devices. Today, the use of X-ray imaging for cargo inspection is becoming more widespread. Such systems are typically made from large welded steel fabrications and are complex and time consuming to install.

SUMMARY OF THE INVENTION

The present invention provides a gantry scanner system comprising a radiation source, detection means which may comprise a plurality of detectors and a support frame supporting the detection means. The support frame may include an elongate support member arranged to support the detection means. The support frame may comprise cable support means arranged to support power cables or signal cables connected to the detectors. The support frame may comprise cover means arranged to cover the support member, the cable support means and the detectors.

The support frame may comprise a plurality of said support members connected together. The support frame may preferably comprise two of said support members connected together at right angles to each other to form a vertical side and a horizontal top of the frame, and a further vertical section connecting one of the support members to a radiation source module. The radiation source module and one of the support members may be movably supported by support means and guide means may be provided to guide the gantry to move along a pre-determined path.

The support member may be of a constant H-shaped cross-section along its length and may comprise a central web and two side sections. The detectors are preferably mounted within a cavity formed by the central web and the two side sections and radiation absorbing means are preferably mounted on an opposite side of the central web to the detectors.

Cable support means may be located on the outer side of at least one of the side sections of the elongate support members and may comprise a cable support tube or conduit mounted on the support section by means of a plurality of tube support brackets. Cover means may comprise a plurality of removable cover sections which can each be removed to allow access to the detectors. A control system and power storage means may be arranged to be connectable to a power supply so that it can be recharged.

The present invention further provides a gantry scanning system comprising a gantry, a radiation source, radiation detectors, a control system and rechargeable power storage means mounted on the gantry, wherein the power storage means is arranged to be connectable to a power supply so that it can be recharged. The system may further comprise guide means defining a path along which the gantry can move, wherein the power storage means are arranged to be connectable to the power supply only when it is in one or more recharging positions on the path. Recharging means are preferably provided at each end of the path so that the power storage means can be recharged in each of two recharging positions.

The control system is also preferably arranged to transmit scan data, obtained by the scanner, wirelessly to a remote station for analysis. The remote station may include display means arranged to display an image generated from the scan data. Further, the control system may be arranged to receive control instructions wirelessly from a remote control station.

BRIEF DESCRIPTION OF THE DRAWINGS

Preferred embodiments of the present invention will now be described by way of example only, with reference to the accompanying drawings, wherein.

DETAILED DESCRIPTION OF THE INVENTION

In the following embodiment of the present invention, a low cost X-ray imaging system is provided which is simple to install and rapid to commission.

Figure 1:
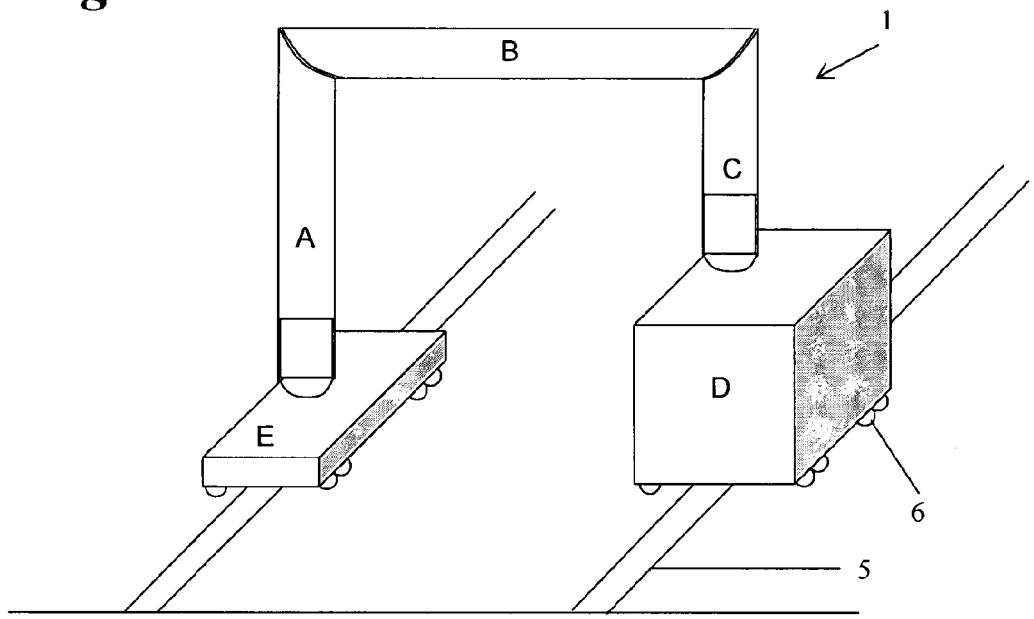
FIG. 1 is a perspective view of a gantry system according to an embodiment of the invention.

A plurality of elongate support members are connected together to form a gantry system as shown in FIG. 1. The gantry 1 comprises two vertical elongate support members A and C which are connected at their top ends at right angles to a horizontal elongate support member B to form an arch. The bottom end of each of the vertical members A and C is connected to and supported on a bogey E, D. One of the vertical support members A supports a multiplicity of individual X-ray detection elements. In a preferred embodiment, the horizontal member B also contains a multiplicity of individual X-ray detection elements. The other vertical support member C provides a structural function, and the bogey D on which it is supported contains the X-ray source, its associated power supplies and control system. The bogeys D and E enable motion of the gantry. The motion of the two bogeys E and D is controlled, such that the bogeys E and D move simultaneously at the same speed and in the same direction to move members A, B and C along rails 5.

In one embodiment, the imaging system is stationary and is operated as a portal. In this case there is no requirement to drive the imaging system backwards and forwards. In the embodiment shown, the imaging system is able to scan backwards and forwards under computer control around a stationary load under inspection. In another embodiment, the control system 44 in Section D is arranged to receive instructions from a remote station, thereby making the gantry 1 entirely wirelessly operated.

In the embodiment shown in FIG. 1, wheels 6 enable motion of the gantry and runners (not shown) located on the underside of bogeys D and E engage with rails 5 and allow movement of the gantry to keep the motion of the gantry uniform along the path defined by the rails 5.

Figure 2:
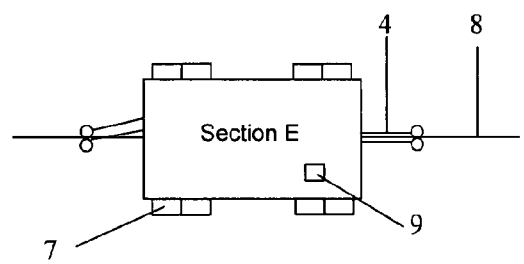
FIG. 2 is a plan view of a section of the gantry system of FIG. 1.

In an alternative embodiment, as shown in FIG. 2, small pneumatic wheels 7 are fitted to the underside of bogeys D and E that run on a level concrete floor. Mechanical guidance is achieved by a metal or plastic guide rail 8 which are fixed to the ground. In this example, a controlling system 9 receives feedback signals from a mechanical sensing arm 4 which is pivotally connected at one end to the bogey E and is engaged with the guide rail 8 at the other end so that it follows the guide rail 8. The control system processes the feedback signals which are indicative of the angle of the sensing arm and outputs instructions to a motor speed control circuit which controls the speed of the wheels 6 to prevent "crabbing" of the system whereby the unit goes off track. Here, the leftmost actuator is out of line, indicating a crabbing possibility.

In another embodiment, guide means defining a path along which the gantry can move are provided in the form of painted lines on the ground which are tracked by a video camera mounted on the bogey. Alternatively, magnetic strips are used which are tracked by a magnetic sensor mounted on the bogey. In yet another embodiment, wheels on bogey Sections E and D engage with rails. Alternative drive schemes may also be appropriate and will be apparent to a person skilled in the art.

Figure 3:
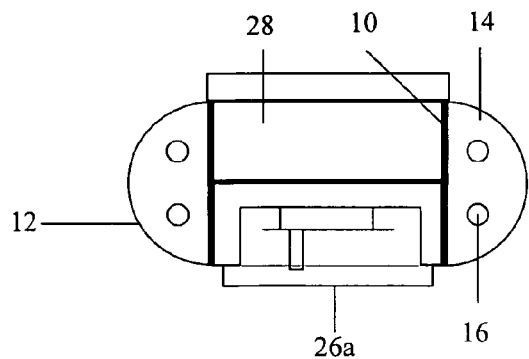
FIG. 3 is a cross-section of elongate support members A and B of FIG. 1.
Figure 3A:
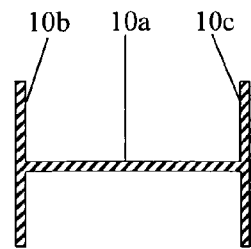
FIG. 3a is a cross-section of an H-shaped girder of FIG. 3.

As shown in FIGS. 3 and 3a, the elongate support members A, B and C are fabricated from a metal girder 10 with an H-shaped cross-section, which comprises a central web 10a and two side sections 10b, 10c. The girder 10 is intrinsically strong and of light weight and may be made of steel or aluminium. Alternatively a rigid composite material such as carbon fibre can be used. To provide further stiffness, an improved aerodynamic profile and weatherproofing, the girder 10 is enclosed by a skin 12, which is moulded carbon fibre composite, moulded glass fibre composite or pressed steel sheet which is welded or glued in place. As can be seen from FIG. 3, the skin surrounds part of the girder to form a generally rounded symmetric shape with one parallel section and two rounded ends. A long aperture 13 is formed in the outer skin 12 along the length of the support member to provide access to the detectors 34.

Figure 4:
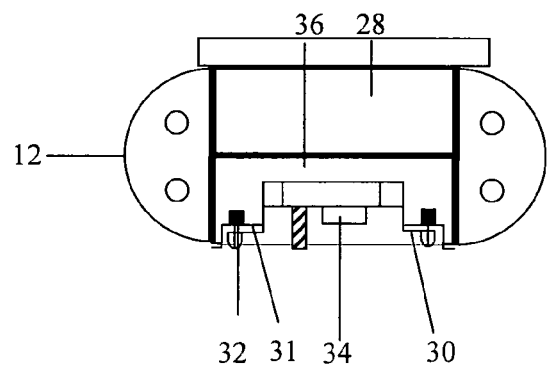
FIG. 4 is a cross-section of elongate support members A and B of FIG. 1 including a detector.

Referring to FIG. 4, X-ray detectors 34 are fitted within a cavity formed between the side sections 10b, 10c extending from a side of the central web 10a of the girder. A moulding 31 that would typically be formed separately to the outer skin 12 is affixed within the cavity on the side of the girder that is not covered by the outer skin. One or more detectors 34 are pre-assembled into each metal or moulded plastic trays 30 which are then mounted onto the moulding 31 by fixing to pre-installed threaded inserts 32. It is advantageous to leave a gap 36 of uniform cross-section between the underside of the tray 30 and the moulding 31 filled with air in order to provide good thermal insulation of the detector components. It is also desirable to insert water absorbing materials, such as silica gel, into these spaces to provide longevity of the detectors 34. Radiation absorbing means 28, which may comprise a lead beam-stop, are mounted on the opposite side of the central web 10a to the detectors 34 between the side sections 10a, 10b.

Figure 5:
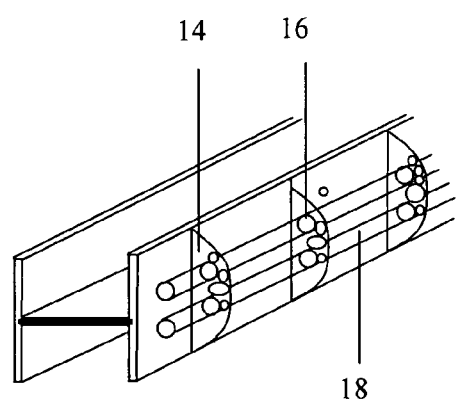
FIG. 5 is a schematic perspective view of the basic structure of elongate support members A, B and C.

The elongate support members A, B, C include support for cables. Prior to attachment of the outer skin 12, a series of thin steel support brackets 14 are welded to the girder 10. As shown in FIG. 5, each support bracket is semi-circular shaped and is affixed to the sides of sections 10b and 10c of the girder 10. The brackets 14 are perforated with holes 16 that have metal or plastic cable support tubes 18 or conduits inserted through them. The tubes 18 extend the full length of the elongate support members and each provide support for either power or signal cables, but not a mixture of power and signal cables. Typically two or three cable tubes 18 may be fitted per bracket 14.

Figure 6:
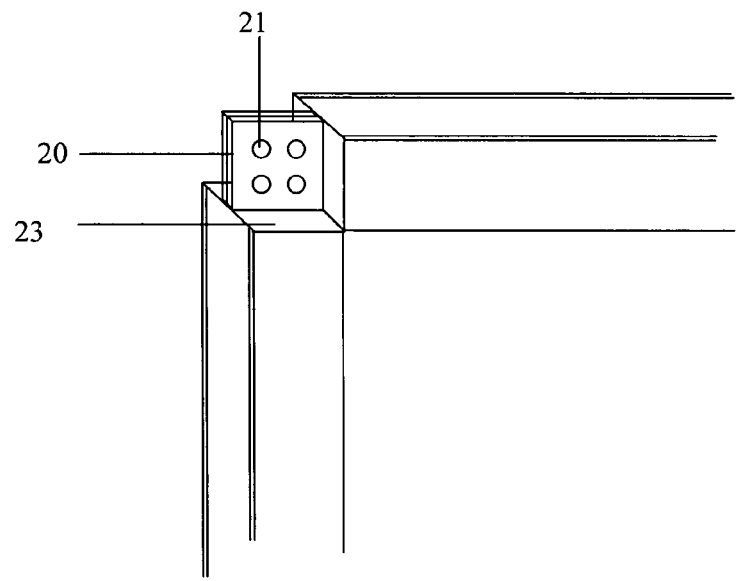
FIG. 6 is a schematic perspective view of a join between elongate support members A and B.

With reference to FIG. 6, an end plate 23 is fitted to the end of the girder of each of the support members A, B and C. A series of joining plates 20 are welded at right angles directly to the girder 10 at the end of Sections A, B and C to provide bolted joining points. Advantageously the joining plates 20 include alignment fixings 21 to ensure accurate assembly of the system prior to tightening up of the main bolts.

Figure 7:
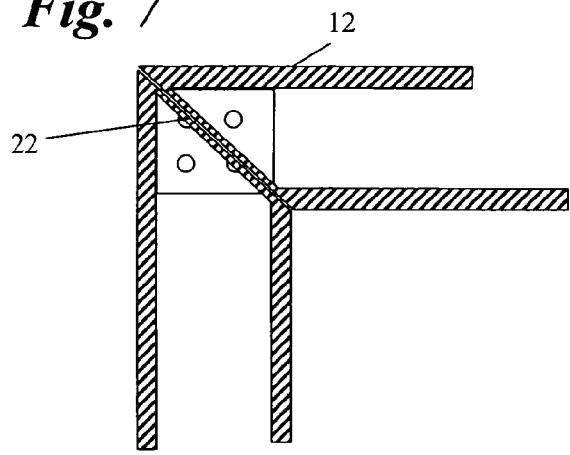
FIG. 7 is a sectional view of a join between elongate support members A and B of FIG. 1 showing the outer skin.
Figure 8:
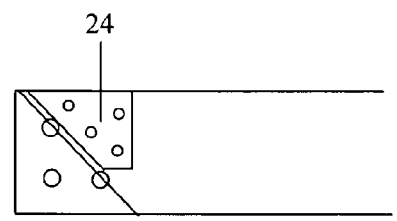
FIG. 8 is a side view of a removable access hatch on elongate support members A, B and C of FIG. 1.

A join between, for example, Sections A and B and between Sections B and C is weatherproofed as shown in FIG. 7. Here, the outer skin 12 at each end of the elongate support member is moulded such that it extends around the joining plate 20 and presents a large area flat face 22 which contacts with the equivalent end face of the other elongate support member when the system is assembled. One of the connecting faces is coated with a suitable adhesive, such as a silicone elastomer, prior to sealing with the other face. As shown in FIG. 8, a removable hatch 24 is provided in each elongate support section over the joint to allow access to the fixings 21 in the joining plates 20 and to allow routing of cables from the support brackets 14 in one of the support member A, B or C to those in the other. The removable hatch 24 is moulded to fit the curvature of the skin 12. The moulded hatch 24 and the skin 12 into which it fits is of a re-entrant design to prevent water ingress. Waterproofing is achieved by using a compressed elastic plastic foam which provides the final seal between the hatch 24 and skin 12. It is advantageous to use quick release fittings to fix the hatch 24 to the elongate support member to minimise repair and installation time. It is also advantageous to fill each of the sections between the outer skin 12 and the internal metal work with an expanded polyurethane foam or other suitable foam material in order to provide thermal insulation between the outer skin 12 and the components within the respective elongate support members A, B and C.

Figure 9A:
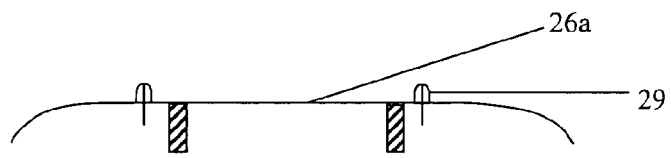
FIG. 9a is a schematic cross-section of a re-entrant cover of the system of FIG. 1.
Figure 9B:
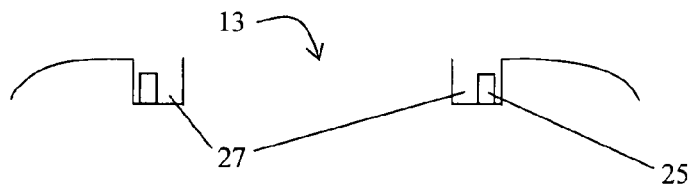
FIG. 9b is a schematic cross-section showing a part of an elongate support member of the system of FIG. 1 for receiving a re-entrant cover.
Figure 9C:
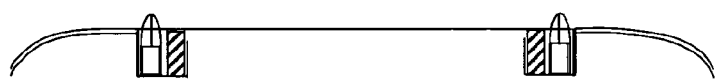
FIG. 9c is a schematic cross-section showing the re-entrant cover of FIG. 9a engaged to a section of a support member for receiving the re-entrant cover of FIG. 9b.

Weatherproof and light proof covers are required to protect the detectors 34 following installation. A re-entrant cover 26, shown in FIG. 9a, is appropriate for this purpose. As shown in FIG. 9b, channels 27 are formed in the skin 12 of the support members at the edge of the aperture 13. Fixtures 25 are located within the channels 27 and are arranged to receive the corresponding fixing 29 which projects down from the top surface 26a of the cover, as shown in FIG. 9a. Quick release fixings are used to allow rapid access for installation and service.

Figure 10:
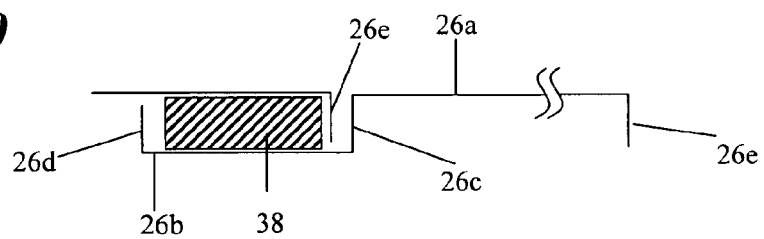
FIG. 10 is a longitudinal cross-section of a re-entrant cover along the length of an elongate support member of FIG. 1.
Figure 11:
FIG. 11 is a perspective view of a re-entrant cover along the length of an elongate support member of FIG. 1.

It is advantageous to use several small covers which overlap, as shown in FIG. 10, to allow rapid removal of the covers when access is required for installation or service purposes because it is easier for service personnel to manoeuvre small covers. Each cover has a substantially flat top surface 26a which is exposed when fitted, and a substantially flat lower surface 26b, spaced from the top surface by a vertical section 26c. A rim 26e projects downwards from one end of the top surface at right angles and a rim 26d projects upwards from the lower surface at right angles to form a trough along one end of the cover. An elastic plastic foam 38 is mounted on the underside the rim of the cover which is compressed when the covers are fitted to prevent environmental ingress. To retain strength, the covers have an arcuate form as shown in FIG. 11. In another embodiment, the cover is hinged along its long edge from fixings that are located on the outside of the outer skin.

Figure 12:
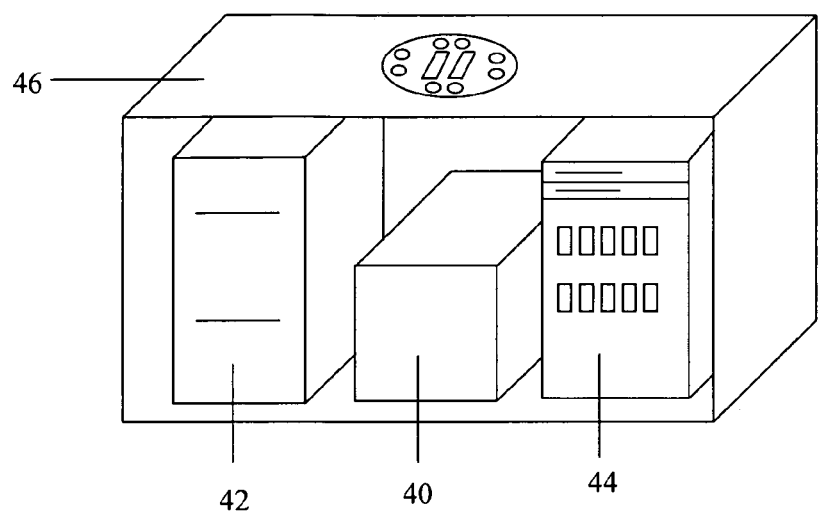
FIG. 12 is a perspective view of part of the gantry system of FIG. 1.
Figure 13:
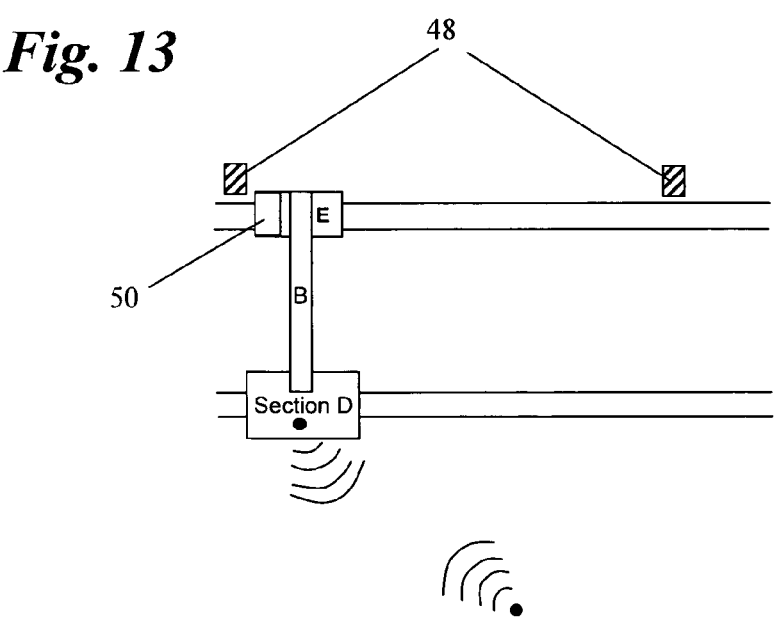
FIG. 13 is a plan view of the gantry system of FIG. 1 including an uninterruptible power supply according to a further embodiment of the invention.

Referring to FIG. 12, bogey D is a cabinet that contains an X-ray linear accelerator 40, an X-ray power supply 42 and control system 44. The cabinet is manufactured using a welded steel framework 46 suitable for supporting the weight of the various components to be installed, and is fitted with weatherproof doors which can be locked shut using keys.

A drawback of many conventional gantry systems is that power and data is typically handled using cables passed through a cable management system such as a caterpillar track system or a cateenery (suspended cable) system. In a preferred embodiment, the power supply 42 includes an uninterruptible power supply 50 (UPS). The control system 44 controls and manages the UPS 50. The UPS 50 is configured to receive mains power from docking stations 48 that are located at either end of the scanning region or guide path as shown in FIG. 12. While the gantry is adjacent to a docking station 48 at each of the two recharging positions, the control system is arranged to establish a connection between the UPS 50 and the docking station 48, in order to allow the power storage means 42 to recharge via the UPS 50. The gantry 1 is self powered while a scan is in progress and works successfully when the time that the system is scanning is less that the time that the system is charging. This is typically the case when individual cargo loads need to be positioned within the imaging zone prior to scanning. The UPS 50 operates to receive power to be recharged only when the power supply 42 is in one or more recharging positions on the path along which the gantry 1 moves.

The control system 44 stores and manages all imaging data relating to each scan and converts the imaging data associated with each scan to an Ethernet packet for transmission wirelessly to a local network access point or to a remote station for analysis. An image generated from the scan data is displayed on a monitor for inspection at the remote station.

I claim:

1. A gantry scanner system comprising a radiation source, a plurality of detectors and a support frame supporting the detectors, wherein the support frame includes an elongate support member arranged to support the detectors, cable support means arranged to support power cables or signal cables connected to the detectors, cover means arranged to cover the support member, the cable support means and the detectors, a rechargeable power storage means mounted on the support frame, and guide means defining a path along which the support frame can move, wherein the power storage means is arranged to be connectable to a stationary power supply so that it can be recharged and wherein the power storage means is arranged to be connectable to the stationary power supply only when it is in one or more recharging positions on the path.

2. A system according to claim 1 wherein the support member is of a constant cross section along its length.

3. A system according to claim 2 wherein the support member comprises a central web and two side sections.

4. A system according to claim 3 wherein the detectors are mounted within a cavity formed by the central web and the side sections.

5. A system according to claim 4 wherein radiation absorbing means are mounted on the opposite side of the central web to the detectors.

6. A system according to claim 3 wherein the support member is of an H-shaped cross-section.

7. A system according to claim 3 wherein the cable support means is located on an outer side of at least one of the side sections.

8. A system according to claim 7 wherein the cable support means comprises a cable support tube mounted on the support member by means of a plurality of tube support brackets.

9. A system according to claim 1 wherein the cover means comprises a plurality of removable cover sections which can each be removed to allow access to the detectors.

10. A system according to claim 1 wherein the support frame comprises a plurality of said support members connected together.

11. A system according to claim 10 wherein the support frame comprises two of said support members connected together at right angles to each other to form a vertical side and a horizontal top of the frame, and a further vertical section connecting one of the support members to a radiation source module.

12. A system according to claim 11 wherein the radiation source module and one of the support members are movably supported by support means and guide means are provided to guide the gantry to move along a predetermined path.

13. A gantry scanning system comprising a gantry, a radiation source, radiation detectors, a control system, a rechargeable power storage means mounted on the gantry, and guide means defining a path along which the gantry can move, wherein the power storage means is arranged to be connectable to a stationary power supply so that it can be recharged and wherein the power storage means is arranged to be connectable to the stationary power supply only when it is in one or more recharging positions on the path.

14. A system according to claim 13 wherein the stationary power supply is provided at each end of the path so that the power storage means can be recharged in each of two recharging positions.

15. A system according to claim 13 wherein the control system is arranged to transmit scan data, obtained by the scanning system, wirelessly to a remote station for analysis.

16. A system according to claim 15 wherein the remote station includes display means arranged to display an image generated from the scan data.

17. A system according to claim 15 wherein the control system is arranged to receive control instructions wirelessly from the remote station.

* * * * *